(12) United States Patent
Wizeman et al.

(10) Patent No.: US 7,931,647 B2
(45) Date of Patent: Apr. 26, 2011

(54) METHOD OF DELIVERING ENERGY TO A LUNG AIRWAY USING MARKERS

(75) Inventors: William J. Wizeman, Mountain View, CA (US); Timothy R. Dalbec, Saratoga, CA (US); Noah Webster, San Francisco, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 1032 days.

(21) Appl. No.: 11/551,639

(22) Filed: Oct. 20, 2006

(65) Prior Publication Data

US 2008/0097424 A1   Apr. 24, 2008

(51) Int. Cl.
    *A61B 18/18* (2006.01)
(52) U.S. Cl. ............................ 606/41; 607/42
(58) Field of Classification Search ............ 606/41, 606/49
    See application file for complete search history.

(56) References Cited

U.S. PATENT DOCUMENTS

| | | |
|---|---|---|
| 1,155,169 A | 9/1915 | Starkweather |
| 1,207,479 A | 12/1916 | Bisgaard |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 4,461,283 A | 7/1984 | Doi |
| 4,462,402 A * | 7/1984 | Burgio et al. .......... 606/129 |
| 4,503,855 A | 3/1985 | Maslanka |
| 4,522,212 A | 6/1985 | Gelinas et al. |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,643,186 A | 2/1987 | Rosen et al. |
| 4,674,497 A | 6/1987 | Ogasawara |
| 4,706,688 A | 11/1987 | Don Michael et al. |
| 4,709,698 A | 12/1987 | Johnston et al. |
| 4,799,479 A | 1/1989 | Spears |
| 4,802,492 A | 2/1989 | Grunstein |
| 4,825,871 A | 5/1989 | Cansell |
| 4,827,935 A | 5/1989 | Geddes et al. |
| 4,862,886 A | 9/1989 | Clarke et al. |

(Continued)

FOREIGN PATENT DOCUMENTS

EP    189329 A3    6/1987

(Continued)

OTHER PUBLICATIONS

Co-pending U.S. Appl. No. 09/244,173.

(Continued)

*Primary Examiner* — Roy D Gibson
*Assistant Examiner* — Benjamin Lee
(74) *Attorney, Agent, or Firm* — Perkins Coie LLP (57) ABSTRACT

An energy delivery device for treating tissue regions in a body conduit, such as a lung airway, may utilize one or more markers, rings, bands, or other visual indicators along an outer surface of the device body. The one or more visual indicators facilitate guidance of the device to effectively and efficiently treat the tissue according to a predetermined axial treatment as well as measure extension of a distal portion of the device, tissue length, and/or treatment length. The predetermined axial treatment may be contiguous, overlapping, or intermittently spaced apart as determined by the marker spacing distance.

23 Claims, 6 Drawing Sheets

U.S. PATENT DOCUMENTS

| | | |
|---|---|---|
| 4,920,978 A | 5/1990 | Colvin |
| 4,955,377 A | 9/1990 | Lennox et al. |
| 4,967,765 A | 11/1990 | Turner et al. |
| 4,976,709 A | 12/1990 | Sand |
| 5,010,892 A | 4/1991 | Colvin et al. |
| 5,019,075 A | 5/1991 | Spears et al. |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,106,360 A | 4/1992 | Ishiwara et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,215,103 A | 6/1993 | Desai |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,394,880 A | 3/1995 | Atlee, III |
| 5,396,887 A | 3/1995 | Imran |
| 5,400,783 A | 3/1995 | Pomeranz et al. |
| 5,409,469 A | 4/1995 | Schaerf |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,425,703 A | 6/1995 | Feiring |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,464,404 A | 11/1995 | Abela et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,500,011 A | 3/1996 | Desai |
| 5,505,728 A | 4/1996 | Ellman et al. |
| 5,505,730 A | 4/1996 | Edwards |
| 5,509,411 A | 4/1996 | Littmann et al. |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,562,619 A | 10/1996 | Mirarchi et al. |
| 5,571,088 A | 11/1996 | Lennox et al. |
| 5,578,067 A | 11/1996 | Ekwall et al. |
| 5,582,609 A | 12/1996 | Swanson et al. |
| 5,588,432 A | 12/1996 | Crowley |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,647,870 A | 7/1997 | Kordis et al. |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,693,078 A | 12/1997 | Desai et al. |
| 5,699,799 A | 12/1997 | Xu et al. |
| 5,707,352 A | 1/1998 | Sekins et al. |
| 5,720,745 A * | 2/1998 | Farin et al. ............... 606/49 |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,728,094 A | 3/1998 | Edwards |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,752,518 A | 5/1998 | McGee et al. |
| 5,755,716 A * | 5/1998 | Garito et al. ............... 606/41 |
| 5,755,753 A | 5/1998 | Knowlton |
| 5,759,158 A | 6/1998 | Swanson |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,795 A | 7/1998 | Bays |
| 5,782,827 A | 7/1998 | Gough et al. |
| 5,782,899 A | 7/1998 | Imran |
| 5,792,064 A | 8/1998 | Panescu et al. |
| 5,795,303 A | 8/1998 | Swanson et al. |
| 5,807,306 A | 9/1998 | Shapland et al. |
| 5,810,807 A | 9/1998 | Ganz et al. |
| 5,814,029 A | 9/1998 | Hassett |
| 5,823,189 A | 10/1998 | Kordis |
| 5,824,359 A | 10/1998 | Khan et al. |
| 5,827,277 A | 10/1998 | Edwards |
| 5,833,632 A | 11/1998 | Jacobsen et al. |
| 5,836,946 A | 11/1998 | Diaz et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |

| Patent | Date | Inventor | | Patent | Date | Inventor | |
|---|---|---|---|---|---|---|---|
| 5,871,443 A | 2/1999 | Edwards et al. | | 6,152,899 A | 11/2000 | Farley et al. | |
| 5,871,523 A | 2/1999 | Fleischman et al. | | 6,159,194 A | 12/2000 | Eggers et al. | |
| 5,873,865 A | 2/1999 | Horzewski et al. | | 6,179,833 B1 | 1/2001 | Taylor | |
| 5,876,340 A | 3/1999 | Tu et al. | | 6,183,468 B1 | 2/2001 | Swanson et al. | |
| 5,876,399 A | 3/1999 | Chia et al. | | 6,197,026 B1* | 3/2001 | Farin et al. | 606/49 |
| 5,881,727 A | 3/1999 | Edwards | | 6,198,970 B1 | 3/2001 | Freed et al. | |
| 5,882,346 A | 3/1999 | Pomeranz et al. | | 6,200,311 B1 | 3/2001 | Danek et al. | |
| 5,891,135 A | 4/1999 | Jackson et al. | | 6,200,332 B1 | 3/2001 | Del Giglio | |
| 5,891,136 A | 4/1999 | McGee et al. | | 6,200,333 B1 | 3/2001 | Laufer | |
| 5,891,138 A | 4/1999 | Tu et al. | | 6,210,367 B1 | 4/2001 | Carr | |
| 5,893,847 A | 4/1999 | Kordis | | 6,214,002 B1 | 4/2001 | Fleischman et al. | |
| 5,897,554 A | 4/1999 | Chia et al. | | 6,216,043 B1 | 4/2001 | Swanson et al. | |
| 5,899,882 A | 5/1999 | Waksman et al. | | 6,216,044 B1 | 4/2001 | Kordis | |
| 5,904,651 A | 5/1999 | Swanson et al. | | 6,217,576 B1 | 4/2001 | Tu et al. | |
| 5,904,711 A | 5/1999 | Flom et al. | | 6,235,024 B1 | 5/2001 | Tu | |
| 5,906,636 A | 5/1999 | Casscells, III et al. | | 6,241,727 B1 | 6/2001 | Tu et al. | |
| 5,908,445 A | 6/1999 | Whayne et al. | | 6,251,104 B1 | 6/2001 | Kesten et al. | |
| 5,908,446 A | 6/1999 | Imran | | 6,254,598 B1 | 7/2001 | Edwards et al. | |
| 5,911,218 A | 6/1999 | DiMarco | | 6,258,087 B1* | 7/2001 | Edwards et al. | 606/41 |
| 5,916,235 A | 6/1999 | Guglielmi | | 6,270,476 B1 | 8/2001 | Santoianni et al. | |
| 5,919,147 A | 7/1999 | Jain | | 6,273,907 B1 | 8/2001 | Laufer | |
| 5,921,999 A | 7/1999 | Dileo | | 6,283,988 B1 | 9/2001 | Laufer et al. | |
| 5,928,228 A | 7/1999 | Kordis et al. | | 6,283,989 B1 | 9/2001 | Laufer et al. | |
| 5,935,079 A | 8/1999 | Swanson et al. | | 6,296,639 B1 | 10/2001 | Truckai et al. | |
| 5,941,869 A | 8/1999 | Patterson et al. | | 6,299,633 B1 | 10/2001 | Laufer | |
| 5,951,494 A | 9/1999 | Wang et al. | | 6,322,559 B1 | 11/2001 | Daulton et al. | |
| 5,954,661 A | 9/1999 | Greenspon et al. | | 6,322,584 B2 | 11/2001 | Ingle et al. | |
| 5,954,662 A | 9/1999 | Swanson et al. | | 6,338,727 B1 | 1/2002 | Noda et al. | |
| 5,954,717 A | 9/1999 | Behl et al. | | 6,338,836 B1 | 1/2002 | Kuth et al. | |
| 5,957,842 A | 9/1999 | Littmann et al. | | 6,379,352 B1 | 4/2002 | Reynolds et al. | |
| 5,957,961 A | 9/1999 | Maguire et al. | | 6,409,723 B1 | 6/2002 | Edwards | |
| 5,964,753 A | 10/1999 | Edwards | | 6,411,852 B1* | 6/2002 | Danek et al. | 607/42 |
| 5,964,796 A | 10/1999 | Imran | | 6,416,511 B1 | 7/2002 | Lesh et al. | |
| 5,968,087 A | 10/1999 | Hess et al. | | 6,423,105 B1 | 7/2002 | Iijima et al. | |
| 5,971,983 A | 10/1999 | Lesh | | 6,425,895 B1 | 7/2002 | Swanson et al. | |
| 5,972,026 A | 10/1999 | Laufer et al. | | 6,438,400 B1 | 8/2002 | Beard et al. | |
| 5,979,456 A | 11/1999 | Magovern | | 6,440,129 B1 | 8/2002 | Simpson | |
| 5,980,563 A | 11/1999 | Tu et al. | | 6,442,435 B2 | 8/2002 | King et al. | |
| 5,991,650 A | 11/1999 | Swanson et al. | | 6,460,545 B2 | 10/2002 | Kordis | |
| 5,992,419 A | 11/1999 | Sterzer et al. | | 6,488,673 B1 | 12/2002 | Laufer et al. | |
| 5,993,462 A | 11/1999 | Pomeranz et al. | | 6,493,589 B1 | 12/2002 | Medhkour et al. | |
| 5,997,534 A | 12/1999 | Tu et al. | | 6,496,738 B2 | 12/2002 | Carr | |
| 5,999,855 A | 12/1999 | DiMarco | | 6,514,246 B1 | 2/2003 | Swanson et al. | |
| 6,003,517 A | 12/1999 | Sheffield et al. | | 6,526,320 B2 | 2/2003 | Mitchell | |
| 6,004,269 A | 12/1999 | Crowley et al. | | 6,529,756 B1 | 3/2003 | Phan et al. | |
| 6,006,755 A | 12/1999 | Edwards | | 6,544,226 B1 | 4/2003 | Gaiser et al. | |
| 6,009,877 A | 1/2000 | Edwards | | 6,544,262 B2 | 4/2003 | Fleischman | |
| 6,010,500 A | 1/2000 | Sherman et al. | | 6,547,776 B1 | 4/2003 | Gaiser et al. | |
| 6,014,579 A | 1/2000 | Pomeranz et al. | | 6,547,788 B1 | 4/2003 | Maguire et al. | |
| 6,016,437 A | 1/2000 | Tu et al. | | 6,572,612 B2 | 6/2003 | Stewart et al. | |
| 6,023,638 A | 2/2000 | Swanson | | 6,575,623 B2 | 6/2003 | Werneth | |
| 6,024,740 A | 2/2000 | Lesh et al. | | 6,582,427 B1 | 6/2003 | Goble et al. | |
| 6,029,091 A | 2/2000 | de la Rama et al. | | 6,582,430 B2 | 6/2003 | Hall | |
| 6,033,397 A | 3/2000 | Laufer et al. | | 6,589,235 B2 | 7/2003 | Wong et al. | |
| 6,036,687 A | 3/2000 | Laufer et al. | | 6,606,521 B2 | 8/2003 | Paspa et al. | |
| 6,036,689 A | 3/2000 | Tu et al. | | 6,610,054 B1 | 8/2003 | Edwards et al. | |
| 6,039,731 A | 3/2000 | Taylor et al. | | 6,613,002 B1 | 9/2003 | Clark et al. | |
| 6,045,549 A | 4/2000 | Smethers et al. | | 6,620,159 B2 | 9/2003 | Hegde | |
| 6,045,550 A | 4/2000 | Simpson et al. | | 6,626,903 B2 | 9/2003 | McGuckin, Jr. et al. | |
| 6,050,992 A | 4/2000 | Nichols | | 6,634,363 B1 | 10/2003 | Danek et al. | |
| 6,053,172 A | 4/2000 | Hovda et al. | | 6,638,273 B1 | 10/2003 | Farley et al. | |
| 6,056,744 A | 5/2000 | Edwards | | 6,640,120 B1 | 10/2003 | Swanson et al. | |
| 6,056,769 A | 5/2000 | Epstein et al. | | 6,645,199 B1 | 11/2003 | Jenkins et al. | |
| 6,066,132 A | 5/2000 | Chen et al. | | 6,645,200 B1 | 11/2003 | Koblish et al. | |
| 6,071,279 A | 6/2000 | Whayne et al. | | 6,652,548 B2 | 11/2003 | Evans et al. | |
| 6,071,280 A | 6/2000 | Edwards et al. | | 6,669,693 B2 | 12/2003 | Friedman | |
| 6,071,281 A | 6/2000 | Burnside et al. | | 6,673,068 B1 | 1/2004 | Berube | |
| 6,071,282 A | 6/2000 | Fleischman | | 6,692,492 B2 | 2/2004 | Simpson et al. | |
| 6,083,255 A | 7/2000 | Laufer et al. | | 6,699,243 B2 | 3/2004 | West et al. | |
| 6,092,528 A | 7/2000 | Edwards | | 6,714,822 B2 | 3/2004 | King et al. | |
| 6,102,886 A | 8/2000 | Lundquist et al. | | 6,723,091 B2 | 4/2004 | Goble et al. | |
| 6,119,030 A | 9/2000 | Morency | | 6,743,197 B1 | 6/2004 | Edwards | |
| 6,123,703 A | 9/2000 | Tu et al. | | 6,749,604 B1 | 6/2004 | Eggers et al. | |
| H1905 H | 10/2000 | Hill | | 6,749,606 B2 | 6/2004 | Keast et al. | |
| 6,129,751 A | 10/2000 | Lucchesi et al. | | 6,749,607 B2 | 6/2004 | Edwards et al. | |
| 6,139,527 A | 10/2000 | Laufer et al. | | 6,767,347 B2 | 7/2004 | Sharkey et al. | |
| 6,142,993 A | 11/2000 | Whayne et al. | | 6,770,070 B1* | 8/2004 | Balbierz | 606/41 |
| 6,143,013 A | 11/2000 | Samson et al. | | 6,802,843 B2 | 10/2004 | Truckai et al. | |
| 6,149,647 A | 11/2000 | Tu et al. | | 6,805,131 B2 | 10/2004 | Kordis | |

| | | | |
|---|---|---|---|
| 6,837,888 B2 | 1/2005 | Ciarrocca et al. | |
| 6,840,243 B2 | 1/2005 | Deem et al. | |
| 6,849,073 B2 | 2/2005 | Hoey et al. | |
| 6,852,091 B2 | 2/2005 | Edwards et al. | |
| 6,852,110 B2 | 2/2005 | Roy et al. | |
| 6,866,662 B2 | 3/2005 | Fuimaono et al. | |
| 6,869,437 B1 | 3/2005 | Hausen et al. | |
| 6,872,206 B2 | 3/2005 | Edwards et al. | |
| 6,881,213 B2 | 4/2005 | Ryan et al. | |
| 6,893,436 B2 | 5/2005 | Woodard et al. | |
| 6,893,439 B2 | 5/2005 | Fleischman | |
| 6,895,267 B2 | 5/2005 | Panescu et al. | |
| 6,904,303 B2 | 6/2005 | Phan et al. | |
| 6,917,834 B2 | 7/2005 | Koblish et al. | |
| 6,954,977 B2 | 10/2005 | Maguire et al. | |
| 7,027,869 B2 | 4/2006 | Danek et al. | |
| 7,043,307 B1 | 5/2006 | Zelickson et al. | |
| 7,104,987 B2 | 9/2006 | Biggs et al. | |
| 7,118,568 B2 | 10/2006 | Hassett et al. | |
| 7,122,033 B2 | 10/2006 | Wood | |
| 7,186,251 B2 | 3/2007 | Malecki et al. | |
| 7,198,635 B2 | 4/2007 | Danek et al. | |
| 7,200,445 B1 | 4/2007 | Dalbec et al. | |
| 7,425,212 B1 | 9/2008 | Danek et al. | |
| 7,556,624 B2 | 7/2009 | Laufer et al. | |
| 2002/0072737 A1 | 6/2002 | Belden et al. | |
| 2002/0091379 A1* | 7/2002 | Danek et al. | 606/32 |
| 2002/0111617 A1 | 8/2002 | Cosman et al. | |
| 2002/0123748 A1 | 9/2002 | Edwards et al. | |
| 2002/0147391 A1 | 10/2002 | Morency | |
| 2002/0173785 A1 | 11/2002 | Spear et al. | |
| 2003/0050631 A1 | 3/2003 | Mody et al. | |
| 2003/0065371 A1 | 4/2003 | Satake | |
| 2003/0233099 A1* | 12/2003 | Danaek et al. | 606/96 |
| 2004/0010289 A1* | 1/2004 | Biggs et al. | 607/2 |
| 2004/0031494 A1 | 2/2004 | Danek et al. | |
| 2004/0153056 A1 | 8/2004 | Muller et al. | |
| 2004/0182399 A1 | 9/2004 | Danek et al. | |
| 2004/0193243 A1 | 9/2004 | Mangiardi et al. | |
| 2004/0243123 A1* | 12/2004 | Grasso et al. | 606/41 |
| 2004/0249401 A1 | 12/2004 | Rabiner et al. | |
| 2005/0010138 A1 | 1/2005 | Mangiardi et al. | |
| 2005/0010270 A1 | 1/2005 | Laufer | |
| 2005/0096644 A1 | 5/2005 | Hall et al. | |
| 2005/0154386 A1 | 7/2005 | West et al. | |
| 2005/0182431 A1 | 8/2005 | Hausen et al. | |
| 2005/0203503 A1 | 9/2005 | Edwards et al. | |
| 2005/0240176 A1 | 10/2005 | Oral et al. | |
| 2005/0272971 A1* | 12/2005 | Ohnishi et al. | 600/101 |
| 2006/0062808 A1 | 3/2006 | Laufer et al. | |
| 2006/0089637 A1 | 4/2006 | Werneth et al. | |
| 2006/0135953 A1 | 6/2006 | Kania et al. | |
| 2006/0200121 A1 | 9/2006 | Mowery | |
| 2006/0205996 A1 | 9/2006 | Presthus et al. | |
| 2006/0247617 A1 | 11/2006 | Danek et al. | |
| 2006/0247618 A1 | 11/2006 | Kaplan et al. | |
| 2006/0247619 A1 | 11/2006 | Kaplan et al. | |
| 2006/0247746 A1 | 11/2006 | Danek et al. | |
| 2007/0100390 A1 | 5/2007 | Danaek et al. | |
| 2007/0106292 A1 | 5/2007 | Kaplan et al. | |
| 2007/0106296 A1 | 5/2007 | Laufer et al. | |
| 2007/0118184 A1 | 5/2007 | Danek et al. | |
| 2007/0123958 A1 | 5/2007 | Laufer | |
| 2007/0123961 A1 | 5/2007 | Danek et al. | |
| 2009/0018538 A1 | 1/2009 | Webster et al. | |
| 2009/0043301 A1 | 2/2009 | Jarrard et al. | |
| 2009/0069797 A1 | 3/2009 | Danek et al. | |

FOREIGN PATENT DOCUMENTS

| | | |
|---|---|---|
| EP | 908713 A1 | 4/1999 |
| EP | 908150 B1 | 5/2003 |
| EP | 1297795 B1 | 8/2005 |
| FR | 2659240 B1 | 7/1997 |
| JP | 7289557 A2 | 11/1995 |
| RU | 2053814 C1 | 2/1996 |
| RU | 2091054 C1 | 9/1997 |
| WO | WO-8911311 A1 | 11/1989 |
| WO | WO-9304734 A1 | 3/1993 |
| WO | WO-9502370 A3 | 1/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9844854 A1 | 10/1998 |
| WO | WO-9852480 A1 | 11/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9934741 A1 | 7/1999 |
| WO | WO-9944506 A1 | 9/1999 |
| WO | WO-9945855 A1 | 9/1999 |
| WO | WO-0051510 A1 | 9/2000 |
| WO | WO-0103642 A1 | 1/2001 |
| WO | WO 2006052940 A2 * | 5/2006 |

OTHER PUBLICATIONS

Co-pending U.S. Appl. No. 09/095,323.

Simon R. Johnson et al., Synthetic Functions of Airway Smooth Muscle in Asthma, Trends Pharmacol. Sci., Aug. 1997, 18(8), 288-292.

Macklem P.T., Mechanical Factors Determining Maximum Bronchoconstriction, European Respiratory Journal, Jun. 1989, 6, 516s-519s.

James C. Hogg, The Pathology of Asthma, APMIS, Oct. 1997, 105(10), 735-745.

Dierkesmann et al., Indication and Results of Endobronchial Laser Therapy, Lung, 1990, 168, 1095-1102.

Netter, F.H., Respiratory System: A Compilation of Paintings Depicting Anatomy and Embryology, Physiology, Pathology, Pathophysiology, and Clinical Features and Treatment of Diseases, In The CIBA Collection of Medical Illustrations M.B. Divertie, ed., Summit: New Jerse, 1979, vol. 7, 119-135.

Provotorov et al., The Clinical Efficacy of Treating Patients with Nonspecific Lung Disease by Using Low-energy Laser Irradiation and Intrapulmonary Drug Adminstriation, ISSN: 0040-3660., Terapevticheskii Arkhiv (USSR), 1991, 63 (12), 18-23.

Vorotnev et al., Low energy treatment of chronic obstructive bronchitis in a general rehabilitation center, ISSN: 0040-3660., Terapevticheskii Arkhiv, 1997, 69 (3), 17-19.

Wiggs B.R. et al., On the Mechanism of Mucosal Folding in Normal and Asthmatic Airways, J. Appl. Physiol., Dec. 1997, 83(6), 1814-1821.

Ivaniuta O. M. et al., Effect Of Low-Power Laser Irradiation Of Bronchial Mucosa On The State Of Systemic And Local Immunity In Patients With Chronic Bronchitis, Problemy Tuberkuleza, 1991, 6, 26-29.

U.S. Appl. No. 11/255,769, filed Oct. 21, 2005, Danek et al.

Co-pending U.S. Appl. No. 12/640,644, filed Dec. 17, 2009, Inventor Jerry Jarrard.

PCT International search report for application No. PCT/US07/80736 mailed on Mar. 13, 2008, 1 page.

* cited by examiner

METHOD OF DELIVERING ENERGY TO A LUNG AIRWAY USING MARKERS

BACKGROUND OF THE INVENTION

Asthma is a disease in which bronchoconstriction, excessive mucus production, and inflammation and swelling of airways occur. This causes widespread variable airflow obstruction which makes it difficult for an asthma sufferer to breathe. Asthma is a chronic disorder, primarily characterized by persistent airway inflammation. Asthma is further characterized by acute episodes of additional airway narrowing via contraction of hyper-responsive airway smooth muscle.

Asthma is traditionally managed pharmacologically by: (1) long term control through use of anti-inflammatories and long-acting bronchodilators and (2) short term management of acute exacerbations through use of short-acting bronchodilators. Both of these approaches require repeated and regular use of prescribed drugs, which often present difficulties in patient compliance. High doses of corticosteroid anti-inflammatory drugs can have serious side effects that require careful management. In addition, some patients are resistant to steroid treatment. The difficulty of avoiding stimulus that triggers asthma is also a common barrier to successful asthma management. As such, current management techniques are neither completely successful nor free from side effects.

Presently, a new treatment for asthma is showing promise. This treatment comprises the application of energy to the airway tissue. This treatment is described in more detail in commonly assigned U.S. Pat. Nos. 6,411,852; 6,634,363; 7,027,869; 7,104,987 and U.S. Publication No. 2005/0010270, each of which is incorporated herein by reference.

The application of energy to airway tissue, when performed via insertion of a treatment device into the bronchial passageways, requires navigation through tortuous anatomy as well as the ability to treat a variety of sizes of bronchial passageways. As discussed in the above referenced patents and applications, use of a radio frequency (RF) energy delivery device provides one mechanism for treating tissue within the bronchial passageways.

Figure 1:
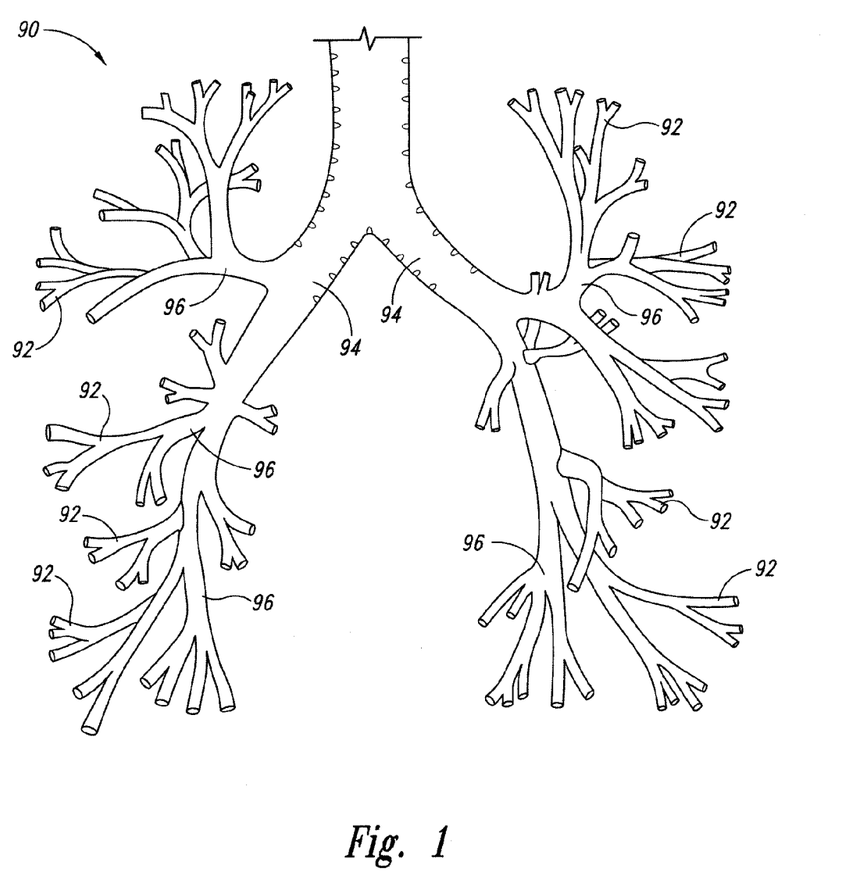
FIG. 1 is an illustration of the airways within a human lung.

FIG. 1 illustrates a bronchial tree 90. As noted herein, devices treating areas of the lungs desirably have a construction that enables navigation through the tortuous passages. As shown, the various bronchioles 92 decrease in size and have many branching segments 96 as they extend into the right and left bronchi 94. Accordingly, an efficient treatment utilizes devices that are able to treat airways of varying sizes as well as function properly when repeatedly deployed after navigating through the tortuous anatomy.

In addition to considerations of navigation and site access, there exists the matter of device orientation at the treatment site. The treatment devices generally make contact or are placed in close proximity to the target tissue. However, in utilizing the treatment devices in a patient, visibility of the energy delivery element, particularly depth perception, within the lung airways may be relatively limited as viewed from an imaging lens of an access device, such as a bronchoscope or endoscope. Limited visibility combined with a variety of other factors, including airway movement due to patient breathing, coughing, and/or wheezing (tidal motion) as well as movement of the access device, may make it difficult to ensure desired axial treatment of the lung airways with the energy delivery device.

For example, in procedures where a relatively long region of tissue is to be treated (e.g., longer than a length of the energy delivery element), difficulty in ascertaining the amount of tissue being treated may result in over-treatment of the same region or non-treatment of the target region. In particular, as the energy delivery element is translated from a first region to a second region and so on, portions of the target tissue may be over-treated or skipped entirely. Additionally, such conditions may result in slower procedures that increase total procedure time and patient discomfort.

In view of the above, methods and devices are desired for treating tortuous anatomy such as the bronchial passages which enable a user to effectively and efficiently treat tissue and relocate an energy delivery device along one or more portions of the tissue.

SUMMARY OF THE INVENTION

In treating tissue regions, such as within the lungs, a treatment device may utilize an elongate sheath or shaft having a plurality of markers, rings, bands, or other visual indicators along an outer surface thereof so as to facilitate guidance of the device to effectively and efficiently treat the tissue according to a predetermined axial treatment. The predetermined axial treatment may be contiguous (adjacent), overlapping, intermittently spaced apart (gapping), or a combination thereof as determined by the marker spacing, and as desired. The visual indicators may also serve as a mechanism for measuring a depth of the treatment device, the tissue length, and/or treatment length, as further described below.

In one aspect of the present invention, an energy delivery device such as an RF electrode basket may be advanced within a working channel of an access device, such as a bronchoscope or endoscope, until a final proximal marker, e.g., a fourth mark, is extended outside the access device, such that the electrode basket, or at least a proximal insulation thereof, and the markers are visible via an imaging lens in the access device. The electrode basket may be deployed into contact against the tissue to be treated and then activated. The treatment device may then be pulled proximally until the next adjacent mark, e.g., a third mark, is reached. This process of activation and pulling proximally may be repeated until a last mark is reached providing for a contiguous and/or continuous axial treatment length of the tissue.

In another aspect of the present invention, the treatment device which may be used in a body conduit, cavity, passageway, or lumen, such as a lung airway, may generally comprise an elongate body, an energy delivery element, and one or more visual indicators. The elongate body comprises a proximal portion with a proximal end and a distal portion with a distal end. The energy delivery element may be disposed at the distal end of the elongate body. The one or more visual indicators may be disposed on the distal portion of the elongate body. Significantly, the visual indicators are separated by a predetermined spacing distance so as to provide the desired predetermined axial treatment in the body conduit or cavity.

In yet another aspect of the prevent invention, the treatment device may comprise a radio frequency energy delivery device for use in a lung airway so as to treat asthma. The device comprises an elongate body having a proximal portion with a proximal end and a distal portion with a distal end. A RF electrode is disposed at the distal end of the elongate body. A plurality of visual indicators are disposed on the distal portion of the elongate body, wherein the visual indicators are separated by a predetermined spacing distance so as to provide a predetermined axial treatment in a lung airway so as to treat asthma.

In a further aspect of the present invention, one method for using the treatment device to deliver energy may generally comprise positioning the access device having a visualization element within a lung airway so as to access airways that are typically 3 mm (or smaller) to 10 mm (or larger) in diameter, as can be properly viewed with direct real-time visualization. The access device may then be stabilized or anchored. The energy delivery device is advanced within the access device so that at least one visual indicator disposed on a distal portion of the energy delivery device and proximal an energy element delivery element disposed on a distal end of the energy delivery device is positioned outside the access device as verified with the visualization element. The visual indicators in turn will provide the desired predetermined axial treatment in the lung airway with the energy delivery element relative to the access device.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

It will be appreciated that the examples below discuss uses in the airways of the lungs. However, unless specifically noted, the devices and methods described herein are not limited to use in the bronchial passageways. Instead, such devices and methods may have applicability in various parts of the body, such as the upper respiratory tract, trachea, esophagus, urethra, ureter, digestive tract, cardiovascular system, circulatory system, arthroscopic, brain, liver, etc. Moreover, the present invention may be used in various procedures where the benefits of the device are desired.

Generally, in treating tissue regions within the lungs, the treatment device may utilize an elongate body, such as tubular sheath, shaft, or catheter, having a plurality of markers, rings, bands, or other visual indicators (e.g., circular or otherwise) along an outer surface thereof. The plurality of visual indicators facilitate guidance of the device to effectively and efficiently treat the tissue according to a predetermined axial treatment. The predetermined axial treatment may be contiguous, overlapping, or intermittently spaced apart treatment of the lung airway walls with the energy delivery element(s). The plurality of visual indicators may also serve as a mechanism to measure a depth of the device, tissue length, airway segment length, and/or treatment length.

In one example of operation, the treatment device, such as an RF electrode basket assembly, may be advanced within a working channel of an access device, such as a bronchoscope, until a final proximal marker is extended distally from the access device while under direct real-time visualization. With the treatment device and the markers visible through the access device, the electrode basket assembly may be deployed against the tissue to be treated and activated. The treatment device may then be pulled proximally relative to the access device until the next adjacent marker is reached. The treatment device may then be activated to treat the portion of tissue adjacent to the previously treated portion without overlap (i.e., over-treatment of the same region) or separation (i.e., non-treatment of target tissue) between the adjacent portions of treated tissue. This process of activation and pulling proximally may be repeated until the last mark is reached providing for a continuous axial treatment where the target tissue regions are neither over-treated nor skipped.

Figure 2:
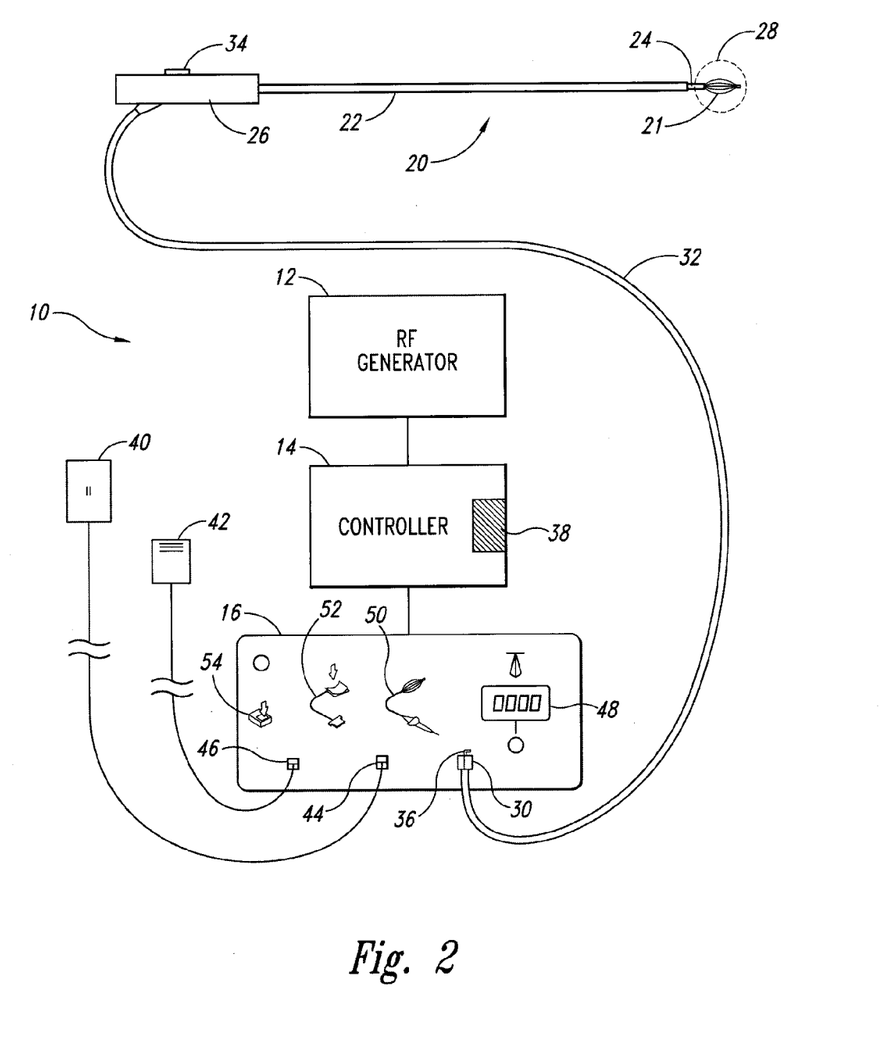
FIG. 2 illustrates a schematic view of a treatment system for delivering energy to tissue utilizing an expandable electrode basket.

Referring now to FIG. 2, a schematic diagram of one example of a treatment system 10 for delivering therapeutic energy to tissue of a patient is illustrated. The system 10 comprises a power supply having an energy generator 12, a controller 14 coupled to the energy generator 12, and a user interface surface 16 in communication with the controller 14. The system 10 further includes an energy delivery device 20, a return electrode 40 (if the system 10 employs a mono-polar RF configuration), and foot actuation pedal(s) 42. It will be appreciated that the above depictions are for illustrative purposes only and do not necessarily reflect the actual shape, size, or dimensions of the system 10 or device 20. This applies to all depictions hereinafter.

The system 10 depicted in FIG. 2 shows the user interface portion 16 having one or more connections 36, 44, 46 for the device 20, the return electrode 40 (optional), and the actuation pedal(s) 42 (optional) respectively. The user interface 16 may also include visual prompts 48, 50, 52, 54 for user feedback regarding setup or operation of the system 10. The user interface 16 may also employ graphical representations of components of the system 10, audio tone generators, as well as other features to assist the user with system operation.

The controller 14 may be configured to deliver RF energy in either a mono-polar or bi-polar configuration. In many variations of the system 10, the controller 14 may include a processor 38 that is generally configured to accept information from the system and system components, and process the information according to various algorithms to produce control signals for controlling the energy generator 12. The processor 38 may also accept information from the system 10 and system components, process the information according to various algorithms and produce information signals that may be directed to the visual indicators, digital display or audio tone generator of the user interface in order to inform the user of the system status, component status, procedure status or any other useful information that is being monitored by the system. The processor 38 of the controller 14 may be a digital IC processor, analog processor, or any other suitable logic or control system that carries out the control algorithms.

Detailed descriptions on the processor 38, user interface 16, and safety algorithms that are useful for the treatment of asthma as discussed above may be found in commonly assigned U.S. patent application Ser. No. 11/408,688, filed Apr. 21, 2006, entitled CONTROL METHODS AND DEVICES FOR ENERGY DELIVERY, which is incorporated herein by reference.

It is understood that the device 20 of the present invention may be used with a variety of systems 10, having the same or different components as described in FIG. 2. For example, although the device 20 is described with reference to RF energy delivery systems 10, variations of the device and system may include light energy sources, laser systems, resistive heating systems, infrared heating elements, microwave energy systems, focused ultrasound, cryo-ablation, radiation, electrical stimulation, or any other energy delivery system or configuration.

The energy delivery device 20 may include a flexible tubular sheath 22, an elongate shaft 24 (in this example, the shaft 24 extends out from the distal end of the sheath 22), and a handle or other optional operator interface 26 secured to a proximal end of the sheath 22. The distal portion of the device 20 includes an energy transfer element 28 for applying energy to the tissue of interest. The energy transfer element 28, such as an expandable electrode basket, may be advanced into and through the patient body in an atraumatic low profile configuration. Upon reaching the designed tissue region to be treated, the energy transfer element 28 may be expanded or reconfigured into a treatment configuration which facilitates contact of the element 28 against the tissue to be treated. In one example, the energy transfer element 28 may be reconfigured via a pull wire 21 routed proximally through elongate shaft 24 and/or flexible sheath 22 and affixed to a handle 26 and actuated with a slide mechanism 34.

Additionally, the device 20 may includes a connector 30 common to such energy delivery devices. The connector 30 may be integral to the end of a cable 32 coupled to the handle 26 or the connector 30 may be fitted to receive a separate cable 32. In any case, the device 20 is configured for attachment to the power supply via some type of connector or adaptor plug 30. The elongate shaft 24 and/or flexible sheath 22 may also be configured and sized to permit passage through a working channel of a commercially available bronchoscope or endoscope. However, the device 20 may also be advanced into a body conduit or cavity with or without a steerable catheter, in a minimally invasive procedure, in an open surgical procedure, or with or without the guidance of various vision or imaging systems.

The devices 20 of the present invention will have a sufficient length and/or diameter and/or flexibility to access the tissue targeted for treatment. For example, treating airways as small as 3 mm in diameter may utilize the flexible sheath 22 and/or elongate shaft 24 which is sufficiently long and sized in diameter to reach deep into the lungs to treat the airways. Generally the device shaft 24 and/or sheath 22 will have a length in range from about 0.5 feet to about 8.0 feet and an expanded basket diameter 28 in a range from about 1 mm to about 25 mm, more preferably from about 3 mm to about 10 mm. However, it is noted that this example is merely illustrative and is not limiting in dimension or flexibility.

Figure 3A:
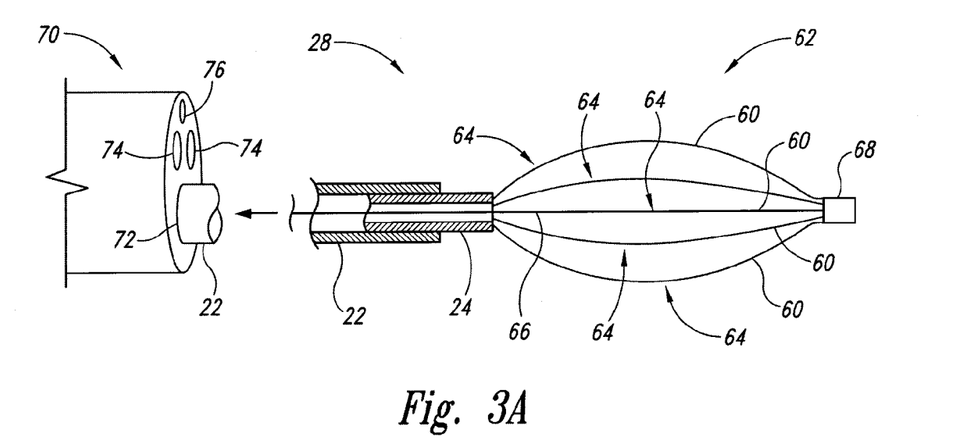
FIG. 3A illustrates a side view of the treatment device of FIG. 2 extending distally from a bronchoscope, wherein the device has an active distal end for treating tissue using energy delivery.

Referring now to FIG. 3A, an example of an energy transfer device 28 is illustrated as an expandable electrode basket. The device 28 has one or more legs 60 configured in the form of a basket 62 converging to an atraumatic common distal tip 68. The basket 62 may reconfigure from an atraumatic low profile shape to an expanded or deployed configuration to facilitate contact against the tissue walls of a body conduit, cavity, passageway, or lumen, such as a lung airway wall. Examples of such devices are described in greater detail in commonly assigned U.S. Publication No. 2003/0233099, which is incorporated herein by reference.

The one or more legs 60 may be configured into the basket shape 62 such that the legs 60 may expand radially during operation to a working diameter as described above that will achieve contact between the legs 60 having active electrode regions 64 and the airway walls. The legs 60 may also include temperature sensors for tissue temperature feedback to the controller 14. In this configuration, four legs 60 are shown, however any number of legs 60 may be utilized to form the basket 62 (e.g., 2, 3, 4, 5, 6, 7, 8, 9, 10, etc.).

As illustrated in FIG. 3A, a pull wire 66 may extend through a lumen of the elongate shaft body 24, to which the basket 62 may be directly mounted. Pull wire 66 may be utilized to deliver energy to the active electrodes 64 and/or assist basket 62 in expanding into its deployed treatment configuration. The treatment device 62 may optionally be delivered to a treatment site directly through the elongate delivery sheath or sleeve body 22. In still other embodiments, pull wire 66 may be omitted entirely in which case basket 62 may be expanded or deployed by utilizing one or more legs 60 which are fabricated as elastic, super-elastic, or shape memory alloys (e.g., nickel-titanium alloys) which may self-expand from a compressed configuration when removed from the elongate sheath 22. In summary, basket 62 may expand upon activation by the user or it may automatically expand when advanced out of a restraining sheath 22 or when the sheath 22 is withdrawn proximally from the basket 62.

The energy transfer device 28 is shown in association with a bronchoscope access device 70. The elongate shaft 24 and flexible sheath 22 are received within a working channel 72 of the bronchoscope 70. Accordingly, the energy transfer device 28 may be utilized along with an imaging lumen 76 and/or light optical fibers 74 of the bronchoscope 70. The imaging lumen 76 may utilize visualization elements, such as CCD imaging or a camera lens. The bronchoscope 70 may additionally comprise an aspiration lumen (not shown).

Figure 3B:
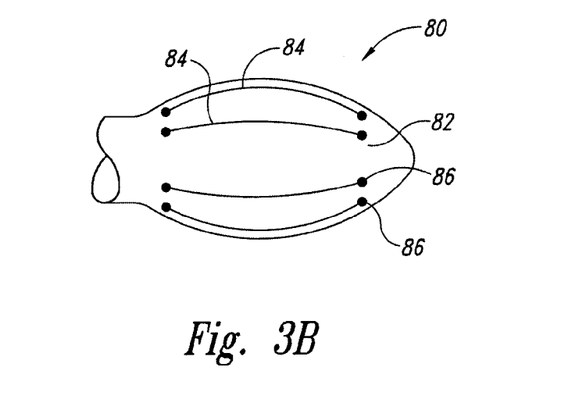
FIG. 3B illustrates a variation of a treatment device comprising an expandable body, such as a balloon, having one or more electrodes disposed along its surface.

Referring now to FIG. 3B, an alternative configuration of the energy transfer device 80 is illustrated. The active member 80 is configured as a body 82 having a set diameter and length. One or more electrodes 84 are shown secured to the body 82 through holes 86 or adhesives or other attachment mechanisms. The electrodes 84 may be oriented axially relative to the body 82 to optimize contact along the tissue walls during treatment. The diameter of active member 80 is set to correspond to that desired for treating a given body lumen or passageway, such as lung airway. Accordingly, body 82 may be configured as an inflatable balloon member, an expandable scaffold member, and the like, where the electrodes 84 will move outward upon body 82 expansion.

Energy delivery devices 28, 80 of wire frames and/or basket configurations will generally have its members (e.g., electrodes) symmetrically deployed. This shape may be round, rounded, or polygonal in cross section. These and other configurations, including asymmetrical active member configurations, are described in detail in U.S. patent application Ser. Nos. 11/255,796, filed Oct. 21, 2005, entitled IMPROVED ENERGY DELIVERY DEVICES AND METHODS and Ser. No. 11/420,438, filed. May 25, 2006, entitled MEDICAL DEVICE WITH PROCEDURE IMPROVEMENT FEATURES, each of which is incorporated herein by reference.

Figure 4:
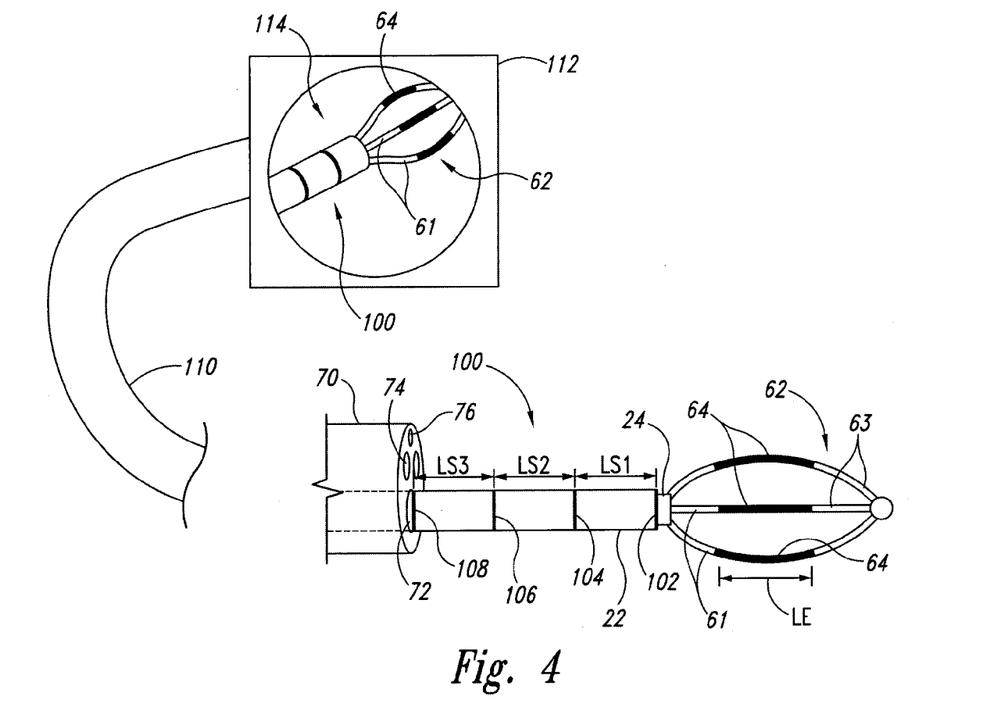
FIG. 4 illustrates an exemplary schematic view of an expandable electrode basket projecting distally from an elongate sheath having one or more markers delineated along its length and a representative image on a monitor corresponding to an image as viewed from the bronchoscope, wherein the spacing distance between each adjacent marker corresponds to a length of the electrodes located on the treatment device.
Figure 5:
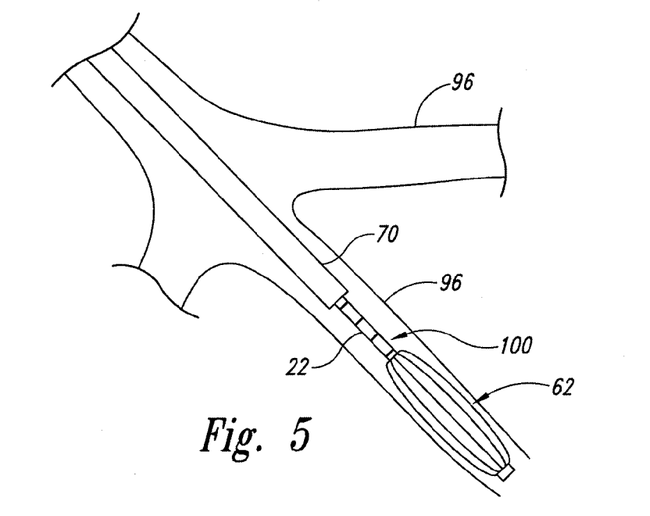
FIG. 5 illustrates the energy delivery device of FIG. 4 advanced into a bronchial airway and positioned for treatment upon the tissue.
Figure 6A:
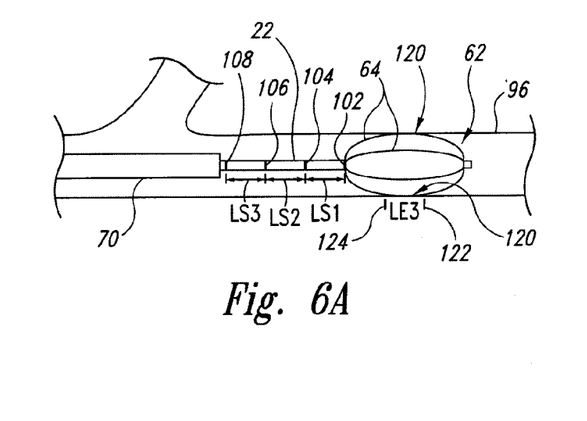
FIGS. 6A and 6B illustrates the treatment device advanced distally within an airway lumen for treating the tissue and the corresponding image from a bronchoscope on a monitor showing the markers along the sheath.
Figure 6B:
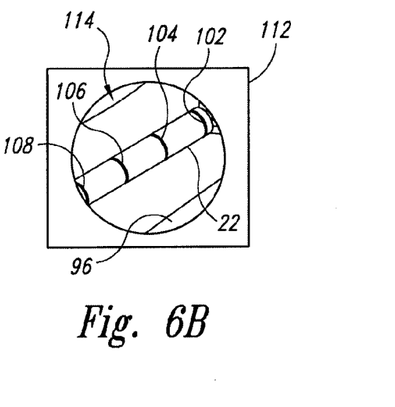

Referring now to FIG. 4, one variation of an exemplary treatment device is shown which facilitates guidance of the expandable electrode basket 62 so as to effectively and efficiently treat tissue as desired, particularly relatively long portions of tissue (e.g., regions of tissue longer than a length of the electrode 64). In this embodiment, the basket 62 is disposed at the distal end of the elongate sheath 22 which in turn is shown projecting distally outward from the bronchoscope 70. One or more visual indicators 100 are disposed along a length of the elongate sheath 22 (or shaft 24), preferably on a distal portion of the sheath 22 and proximal to the basket 62. Visual indicators 100 may generally comprise one or more markers, rings, bands, and the like. For example, a first marker 102 may be positioned proximally of basket 62, a second marker 104 may be positioned proximally of first marker 102, a third marker 106 may be positioned proximally of second marker 104, and a fourth marker 108 may be positioned proximally of third marker 106. In another variation, at least two circular bands or rings may be utilized and in other variations, four circular bands or rings may be utilized. It will be appreciated that any number, type, and/or combination of markers, rings or bands may be utilized in the present invention (e.g., 2, 3, 4, 5, 6, 7, 8, 9, 10, etc.).

Each marker 102, 104, 106, 108 may be uniformly spaced apart from one another with each spacing matching the length of the active electrodes 64 of basket 62. Thus, each spacing between markers 102, 104, 106, 108 may be set to correspond to a length of a active electrode 64 located centrally between proximal and distal insulation regions 61, 63 of the basket leg 60. For instance, active electrodes 64 having a length of 5 mm along basket 62 may provide for a length of 5 mm between markers 102, 104, 106, 108. It will be appreciated that the active electrode length 64 and corresponding marker spacing of 5 mm is illustrative and other lengths fewer than 5 mm or greater than 5 mm may also be utilized as desired. For example, the predetermined spacing distance may range anywhere from about 3 mm to about 30 mm, more preferably in a range from about 5 mm to about 15 mm, depending on the active electrode length, basket leg length, electrode array length parallel to a longitudinal axis of the airway lumen, treatment temperature, time, power, current, voltage, and/or energy settings, and/or polarity configuration.

As mentioned above, in one variation the spacing between these markers 102, 104, 106, 108 may each correspond to a length LE of the active electrodes 64 on basket 62. For instance, a first marker distance LS1 between first marker 102 and second marker 104, a second marker distance LS2 between second marker 104 and third marker 106, and a third marker distance LS3 between third marker 106 and fourth marker 108 may each correspond in length to the length LE of active electrodes 64 on basket 62. Moreover, although four markers are illustrated in this example, fewer than four or more than four markers, as desired, may be utilized along the length of elongate sheath 22 in alternative variations.

Bronchoscope 70 may be electrically coupled 110 to a monitor 112 and/or processor configured to display images 114 received from imaging lumen 76. As represented on monitor 112, the displayed image corresponds to an image as viewed from the perspective of lumen 76 showing basket 62 projected from the elongate sheath 22. Also illustrated are the visual markings 100 positioned along the sheath 22.

Advantageously, the embodiment of FIG. 4 allows for the amount of tissue being treated by the basket 62 to be easily ascertained with reference to the visual markers 100. In particular, markers 100 improve visibility and/or navigation of locating and placing the treatment electrodes 64 so as to reliably and uniformly apply predetermined axial treatments (e.g., continuous activation treatments). This in turn may reduce physician effort or fatigue (e.g., less surgical technique sensitive), total treatment procedure time, and/or patient discomfort and improve procedure efficacy.

Referring now to FIGS. 5 through 8B, the basket 62 and elongate sheath 22 may be deployed from bronchoscope 70 and positioned distally of bronchoscope 70 along the tissue wall of a bifurcated airway 96. In one example of use, basket 62 may be deployed from bronchoscope 70 and advanced distally relative to bronchoscope working channel 72, as shown in FIG. 6A, while visualizing the passage of markers 102, 104, 106, 108 in monitor 112 directly in real-time, as illustrated in FIG. 6B. With basket 62 positioned, it may be expanded into contact against the surrounding tissue wall 96 and the active electrodes 64 may be activated to heat the airway tissue 120 along a treatment length LE3. The treated tissue length LE3, extending between tissue borders 122, 124, may correspond in length to third marker spacing distance LS3 on elongate sheath 22.

Figure 7A:
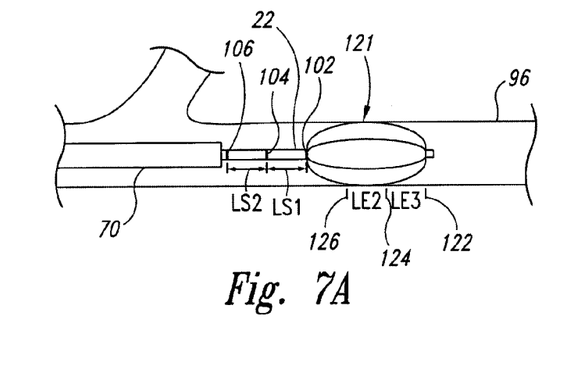
FIGS. 7A and 7B illustrate the treatment device pulled proximally along the tissue by a length corresponding to a length between markers along the sheath such that the treatment device is aligned to an adjacent region of tissue to be treated.
Figure 7B:
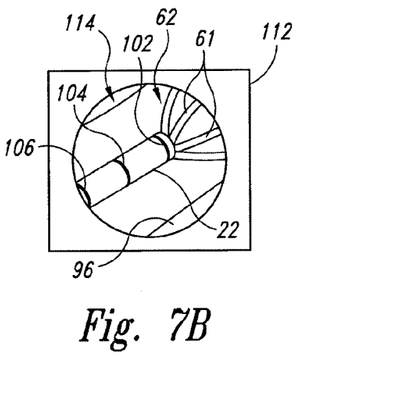

Once the treatment is completed along tissue length LE3, basket 62 may be retracted and withdrawn proximally relative to bronchoscope 70 while visualizing on monitor 112 by one marker length until the fourth marker 108 is no longer visible and third marker 106 is verified as visible in the monitor 112, as shown in FIG. 7B. Moving elongate sheath 22 by such a distance also translates basket 62 proximally by one marker length LS3 and correspondingly translates the active electrodes 64 to an adjacent tissue region proximal to the previously treated tissue length LE3. Once desirably positioned, basket 62 may then again be actuated so as to deploy against the airway wall 96 and activated to heat the airway tissue 121 along a treatment length LE2 which borders treated tissue length LE3 contiguously without overlapping or leaving any gap between the two treated tissue lengths, as shown in FIG. 7A.

Figure 8A:
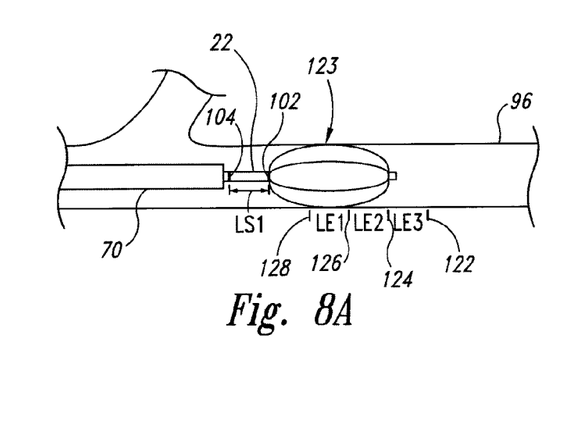
FIGS. 8A and 8B illustrate the treatment device pulled further proximally along the tissue by a length corresponding to a length between markers along the sheath such that the treatment device is aligned to another adjacent region of tissue to be treated.
Figure 8B:
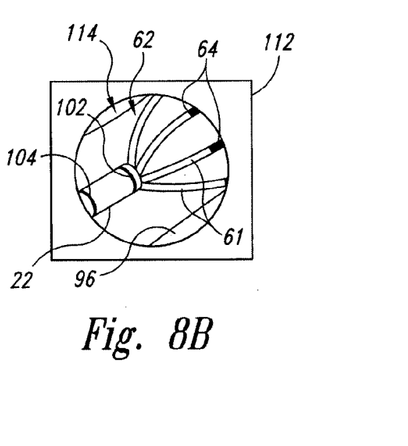

Once the tissue along tissue length LE2 has been treated, basket 62 may once again be retracted and withdrawn proximally relative to bronchoscope 70 by another marker length such that third marker 106 is no longer visible and second marker 104 is verified as visible on the monitor 112, as shown in FIG. 8B. Accordingly, basket 62 is translated proximally by a corresponding distance along the tissue such that the active electrodes 64 are aligned between tissue borders 126 and 128. The basket 62 may then be activated to treat the tissue region 123 along tissue length LE1 which borders treated tissue length LE2, as illustrated in FIG. 8A. This process of deploying, activating, retracting, and pulling proximally may be repeated, as desired, until first marker 102 is reached or by pulling the bronchoscope 70 proximally with respect to the sheath markers 100 and following the above steps relative to the stationary bronchoscope 70. Thus, longer portions of the tissue may be treated as desired.

The resulting treated tissue may be thus formed into a contiguous length of treated tissue (e.g., LE1, LE2, LE3) which avoids over-treating the tissue by avoiding overlapping regions and avoids the formation of gaps between adjacent tissue lengths. Once the treatment is completed, the basket 62 may be withdrawn proximally into the bronchoscope working channel 72 for withdrawal from the patient or advancement into another region of tissue to be treated. Thus, if the length of the active electrode 64 is 5 mm and the corresponding marker lengths LS1, LS2, LS3 are each 5 mm in length, the tissue may be treated in increments of 5, 10, 15, 20 mm or more in a contiguous manner depending upon the desired length of tissue to be treated. The predetermined axial treatment (e.g., LE1, LE2, LE3) may comprise treatment of the lung airways for a length of at least 10 mm, preferably in a range from about 10 mm to about 75 mm, more preferably in a range from about 20 mm to about 30 mm.

It will be appreciated that there are several ways to use the device of the present invention, and as such is not limited by the above example. In an alternative method of use, elongate sheath 22 may be translated distally relative to bronchoscope 70 such that the initial treatment is initiated when first marker 102 is visualized. Accordingly, subsequent portions of tissue may be treated by advancing the basket 62 distally relative to bronchoscope 70 while viewing advancement of the markers on monitor 112. In yet another variation, the elongate sheath 22 and basket 62 may be initially advanced distally until the first marker 102, second marker 104, or third marker 106 is exposed rather than being fully advanced until the fourth marker 108 is exposed. Thus, shorter portions of the tissue may be treated as desired.

Figure 9A:
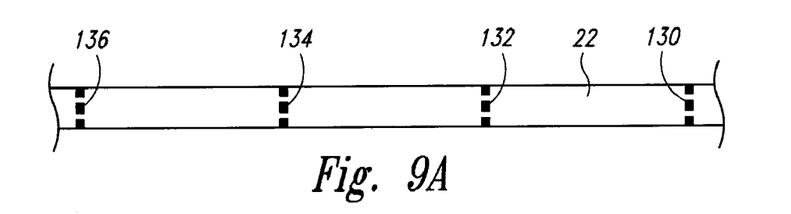
FIG. 9A illustrates a variation of the sheath utilizing dashed markers.
Figure 9B:
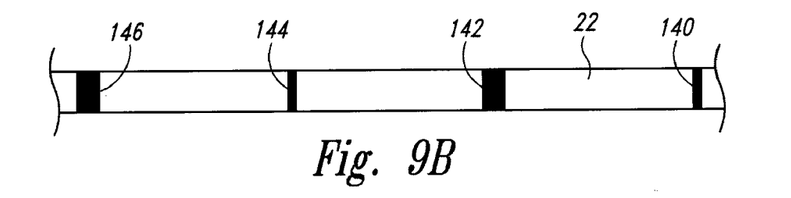
FIG. 9B illustrates another variation of the sheath utilizing non-uniform markers.

Referring now to FIGS. 9A through 9F, although markers 100 may be identical, it will be appreciated that they may also be varied in any number of configurations. For example, FIG. 9A illustrates one variation where the markers 130, 132, 134, 136 may be dashed rather than solid. Another variation is shown in FIG. 9B where the markers may be non-uniform in width, or alternating in width. For instance, markers 140, 144 may have a first width while alternating markers 142, 146 may have a second width larger than the first width.

Figure 9C:
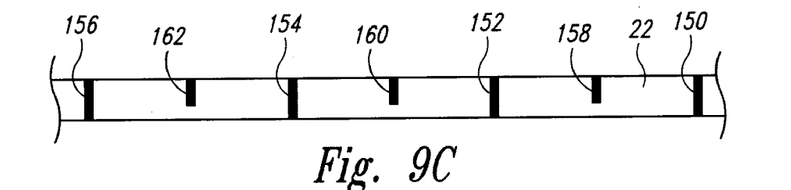
FIG. 9C illustrates another variation of the sheath utilizing markers which have a length between adjacent markers which is less than a length of the electrodes on the treatment device such that overlapping regions of tissue may be treated.

In yet another variation, the markers 150, 152, 154, 156 may be aligned to correspond to the active electrode length, as described above. Additional half markers 158, 160, 162 may be marked at, e.g., intermediate positions between markers 150, 152, 154, 156, to denote positions where portions of tissue may be treated by overlapping the treatment regions, as shown in FIG. 9C.

Figure 9D:
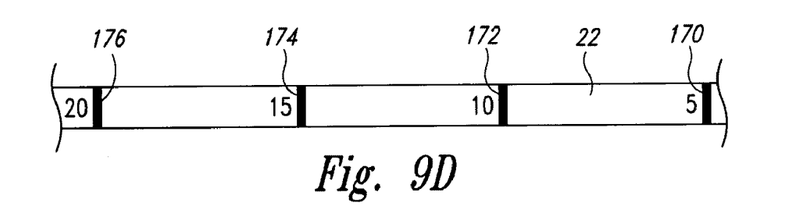
FIG. 9D illustrates yet another variation of the sheath utilizing markers having graduated measurements therealong to provide a visual indication of tissue or treatment length and/or electrode basket depth.

Another variation is illustrated in FIG. 9D where markers 170, 172, 174, 176 may be graduated with length measurements, e.g., 5 mm, 10 mm, 15 mm, 20 mm, etc., much like an endoscope to facilitate measurement of basket 62 insertion depth or to facilitate measurement of the tissue region (e.g., length of the lung airway). In this manner, a portion of tissue or the depth in which the treatment device is advanced may be ascertained by directly visualizing the elongate sheath 22 extending from the stationary bronchoscope 70. Although the measurement values are illustrated in 5 mm increments corresponding to the length of the active electrode 64 on the electrode basket 62, any number of incremental values may be marked and delineated either in a corresponding or even non-corresponding manner with respect to the active electrodes, if so desired.

Figure 9E:
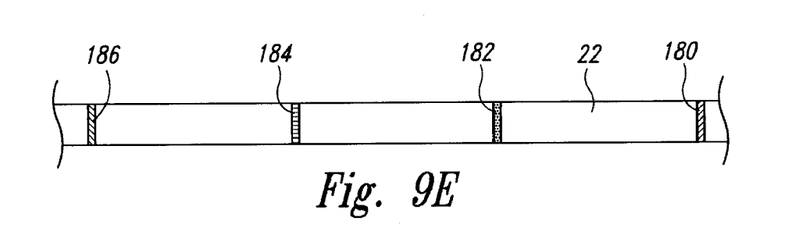
FIG. 9E illustrates yet another variation of the sheath utilizing markers having alternative colors, such as a green marker to indicate treatment device deployment or a red marker to indicate a maximum length of sheath extension.

Referring now to FIG. 9E, an elongate sheath 22 having markers which are in various colors to denote particular features associated with that particular marking is illustrated. Although the markers may be colored in the same color (e.g., black), various colors may be utilized, particularly to indicate predetermined device states. For example, marker 180 may comprise a first color (e.g., green) to indicate that once marker 180 is visible, electrode basket 62 is sufficiently advanced relative to the bronchoscope 70 for expansion and/or activation. Additional markers 182, 184 may also comprise various colors as well while the proximal marker 186 may also be colored in yet another color (e.g., red) as a visual indication that the elongate sheath 22 should not be advanced any further distal into the airway lung.

Figure 9F:
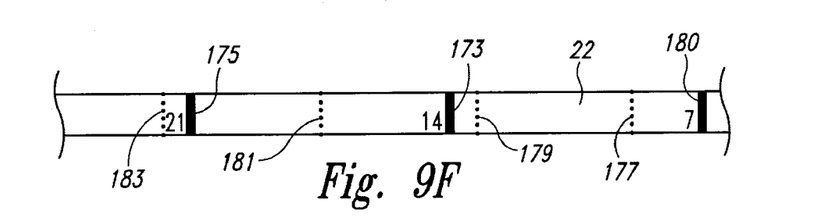
FIG. 9F illustrates still another variation of the sheath utilizing markers which have a length between adjacent markers which is greater than a length of the electrodes on the treatment device such that intermittent regions of tissue may be treated.

In yet another variation, markers 171, 173, 175 (with graduations 7 mm, 14 mm, 21 mm) may have a length between adjacent markers which is greater than a length of the active electrodes 64 of the treatment device so that intermittent regions of tissue may be treated, as shown in FIG. 9F. Still further, the sheath may have a second set of markers 177, 179, 181, 183 that have a different spacing distance, e.g., set to the active electrode 64 length, so that a user may utilize a particular marker set based on a particular anatomy section to be treated.

In these and other variations described herein, each of the markers may be marked on the elongate sheath 22 in various increments and are not limited to just the length of the active electrodes 64, as described above in detail. Moreover, additional markers may be utilized or as few as a single marker may be utilized depending upon the desired visual indications.

The markers may also serve as a safety feature to discourage the pre-mature deployment of the electrode basket 62 within the bronchoscope 70. For example, the first proximal marker may serve this purpose so as to prevent against any electrical discharge from flowing proximally along the sheath 22, shaft 24 and/or bronchoscope 70, which could potentially result in injury or harm to the patient or user. Additionally, the final proximal marker, which may be positioned along sheath 22 up to 75 mm or more, more preferably up to 50 mm or 30 mm, from the electrode basket 62, may also serve as a visual safety feature to ensure against advancing the electrode basket 62 too deep into the patient body (i.e., beyond bronchoscopic vision), which in turn prevents against any patient harm, such as puncturing of the airway wall into the parenchyma, pneumothorax, pneumomediastinum, etc.

In yet another alternative, at least one of the markers may also be aligned with an anatomical landmark within the lung airway to provide not only for alignment of the device but also to facilitate measurement of the lung airway, if so desired. For example, a marker may be aligned with a particular airway bifurcation, colored tissue, cartilage ring, tissue nodule, and the like, so as to ensure against user disorientation due to tidal motion or movement of the access device.

Referring back to FIG. 8B, it will be further appreciated that the markers 102 further allow for user differentiation of the sheath 22 from the insulated electrodes 61, 63, particularly the proximal insulation regions of the basket legs 60. This visualization is important to ensure proper deployment of the basket electrode 62.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, the plurality of visual indicators may be located on the device shaft, the energy delivery device may comprise a non-RF source, and/or the expandable energy device may comprise an inflatable balloon member. Still further, the markers of the present invention may be positioned alternatively or additionally on a proximal portion of the sheath or shaft that extends at least partially outside the access device and patient. Proximal makers may also facilitate quicker and more confident introduction of the shaft into the access device by indicating a measurement of the shaft within the access device. Reference to a singular element, includes the possibility that there are plural of the same elements present. More specifically, as used herein and in the appended claims, the singular forms "a," "an," "said," and "the" include plural referents unless the context clearly dictates otherwise. Therefore, the above description should not be taken as limiting the scope of the invention which is defined by the appended claims.

What is claimed is:

1. A method for delivering energy in a lung airway, the method comprising:
   positioning an access device having a visualization element within a lung airway;
   advancing an energy delivery device within the access device, wherein a plurality of visual indicators disposed on a distal portion of the energy delivery device and proximal an energy delivery element disposed on a distal end of the energy delivery device are positioned outside the access device as verified with the visualization element so as to provide a predetermined axial treatment in the lung airway with the energy delivery element a predetermined distance relative to the access device;
   delivering energy to the lung airway from the energy delivery element at the predetermined distance relative to the access device;
   pulling the energy delivery device in a proximal direction relative to the access device until a next visual indicator disposed on the distal portion of the energy delivery device is verified with the visualization element; and
   repeating the delivering and pulling steps so as to incrementally deliver energy to the lung airway at a plurality of predetermined axial treatment sites relative to the access device.

2. The method of claim 1, wherein the predetermined axial treatment comprises contiguous, overlapping, intermittent, or combination treatment thereof of the lung airway with the energy delivery element.

3. The method of claim 1, wherein the predetermined axial treatment comprises contiguous treatment of the lung airway for a length of at least 10 mm.

4. The method of claim 1, further comprising positioning a last visual indicator disposed on the distal portion of the energy delivery device outside the access device as verified with the visualization element.

5. The method of claim 4, further comprising deploying the energy delivery element outside the access device such that the energy delivery element contacts a wall within a lung airway, and then activating the energy delivery device to deliver the energy to the lung airway.

6. The method of claim 5, further comprising retracting the energy delivery element and pulling the energy delivery device in a proximal direction relative to the access device until a next visual indicator disposed on the distal portion of the energy delivery device is verified with the visualization element.

7. The method of claim 1, further comprising deploying and activating the energy delivery element outside the access device and within the lung airway.

8. The method of claim 7, further comprising retracting the energy delivery element and positioning a second visual indicator disposed on the distal portion of the energy delivery device outside the access device as verified with the visualization element.

9. The method of claim 8, further comprising repeating the deploying, activating, retracting, and positioning steps so as to provide the predetermined axial treatment in the lung airway relative to the access device.

10. The method of claim 1, further comprising preventing pre-mature deployment of the energy delivery element within the access device by visualization of a first visual indicator.

11. The method of claim 1, further comprising preventing distal advancement of the energy delivery element beyond a predetermined distance from the access device by visualization of a last visual indicator.

12. The method of claim 1, further comprising aligning the visual indicator with an anatomical landmark in the lung airway.

13. The method of claim 1, further comprising measuring a length of the lung airway by visual indicator positioning.

14. The method of claim 1, further comprising measuring a depth of the energy delivery element by visual indicator positioning.

15. A method for delivering energy in a lung airway, the method comprising:
   positioning an access device having a visualization element within a lung airway;
   advancing an energy delivery device to a tissue region in the lung airway through the access device, the energy delivery device having a shaft, an energy delivery element disposed on a distal end of the shaft, and a plurality of position indicators along the shaft proximal of the energy delivery element;
   placing a plurality of the position indicators of the energy delivery device outside the access device;
   visualizing at least one of the position indicators positioned outside the access device with the visualization element; and
   verifying an axial position of the energy delivery element in the lung airway relative to the access device based on the visualized position indicator;
   delivering energy to the lung airway from the energy delivery device at the predetermined distance relative to the access device; and
   wherein the position indicators comprise markers spaced apart from each other by a predetermined spacing distance corresponding to an active electrode length of the energy delivery device, and the method further comprises treating the tissue region in the lung airway in a contiguous and/or intermittent pattern with the energy delivery element.

16. The method of claim 15, further comprising treating the tissue region in the lung airway in a contiguous pattern for a length of at least 10 mm.

17. The method of claim 15, further comprising deploying and activating the energy delivery element outside the access device within the lung airway.

18. The method of claim 17, wherein:
- the position indicators include a first indicator adjacent to a second indicator;
- visualizing the position indicators includes visualizing the first indicator outside the access device; and
- the method further comprising moving the energy delivery element in a proximal direction relative to the access device until the second indicator is visualized with the visualization element.

19. The method of claim 18, further comprising repeating the delivering and moving proximal steps to provide a predetermined axial treatment in the lung airway relative to the access device.

20. The method of claim 15, further comprising preventing deployment of the energy delivery element within the access device until the position indicator is visualized.

21. The method of claim 15, further comprising preventing distal advancement of the energy delivery element beyond a predetermined distance from the access device until the position indicator is visualized.

22. The method of claim 15, further comprising aligning at least one of the position indicators with an anatomical landmark in the lung airway.

23. The method of claim 15, wherein the position indicators include a plurality of equally spaced markers, and the method further comprising measuring a length of the lung airway by axially moving the energy delivery device in the lung airway, visualizing at least some of the markers, and recording a number of the markers visualized.

* * * * *